US012791505B2

(12) United States Patent
Kim et al.

(10) Patent No.: US 12,791,505 B2
(45) Date of Patent: Nov. 10, 2026

(54) THERMAL DESORPTION ANALYSIS AUTOMATION SYSTEM AND ANALYSIS METHOD USING SAME

(71) Applicants: WITHTECH INC., Daejeon (KR); SAMSUNG ELECTRONICS CO., LTD., Suwon-si (KR)

(72) Inventors: Ho Chan Kim, Osan-si (KR); Jeong Seok Kim, Osan-si (KR); Young Su Jun, Daejeon (KR); Eung Sun Lee, Hwaseong-si (KR); Seoung Kyo Yoo, Daejeon (KR); Hyun Yul Park, Cheongju-si (KR)

(73) Assignees: SAMSUNG ELECTRONICS CO., LTD., Suwon-si (KR); WITHTECH INC., Daejeon (KR)

( * ) Notice: Subject to any disclaimer, the term of this patent is extended or adjusted under 35 U.S.C. 154(b) by 614 days.

(21) Appl. No.: 18/134,263

(22) Filed: Apr. 13, 2023

(65) Prior Publication Data

US 2023/0333036 A1 Oct. 19, 2023

(30) Foreign Application Priority Data

Apr. 14, 2022 (KR) ........................ 10-2022-0046079

(51) Int. Cl.

*G01N 25/72* (2006.01)
*G01N 1/44* (2006.01)
(Continued)

(52) U.S. Cl.

CPC ............... *G01N 25/72* (2013.01); *G01N 1/44* (2013.01); *G01N 33/0095* (2024.05)

(58) Field of Classification Search

CPC ...... G01N 25/72; G01N 1/44; G01N 33/0095; G01N 35/00; G01N 35/00584; G01N 2035/00346; H01L 22/10
See application file for complete search history.

(56) References Cited

U.S. PATENT DOCUMENTS 5,223,001 A * 6/1993 Saeki ................ H01L 21/67751 414/217
5,482,524 A * 1/1996 Nakano .................. G01N 30/00 96/144
(Continued)

FOREIGN PATENT DOCUMENTS

CN 101236894 A 8/2008
JP H783808 A 3/1995
(Continued)

*Primary Examiner* — Laura Martin Sweeney
*Assistant Examiner* — Anthony W Megna Fuentes
(74) *Attorney, Agent, or Firm* — The Webb Law Firm

(57) ABSTRACT

The present invention relates to a Thermal Desorption analysis automation system including an automation system and an analysis method using the same to quickly perform a wafer defect analysis process. The Thermal Desorption analysis automation system includes a heating device that includes a heater for heating a wafer, an analysis device that receives gas containing contaminants desorbed from the heated wafer and analyzes the gas, a coupling part that is disposed outside a chamber and coupled to the wafer, a wafer transfer device that is provided with an arm transferring the coupling part, and a control unit that controls the wafer transfer device to insert the wafer into the chamber and transfer the wafer in the chamber to the outside.

12 Claims, 6 Drawing Sheets

(51) Int. Cl.

| | |
|---|---|
| ***G01N 33/00*** | (2006.01) |
| ***G01N 35/00*** | (2006.01) |
| *H10P 74/20* | (2026.01) |

(56) References Cited

U.S. PATENT DOCUMENTS

| | | | | |
|---|---|---|---|---|
| 6,602,348 | B1 * | 8/2003 | Rogelstad ......... H01L 21/67109 156/345.31 | |
| 2002/0148974 | A1 | 10/2002 | Hung et al. | |
| 2007/0186776 | A1 * | 8/2007 | Yeatman .................. G01N 1/44 96/4 | |
| 2008/0179006 | A1 * | 7/2008 | Tahara ................ C23C 16/4401 118/729 | |
| 2018/0045697 | A1 | 2/2018 | Suk et al. | |

FOREIGN PATENT DOCUMENTS

| | | | |
|---|---|---|---|
| JP | H08250567 | A | 9/1996 |
| JP | H915209 | A | 1/1997 |
| JP | H943211 | A | 2/1997 |
| JP | H10267802 | A | 10/1998 |
| JP | H11287743 | A | 10/1999 |
| JP | 2000264438 | A | 9/2000 |
| JP | 2008192642 | A | 8/2008 |
| JP | 201751326 | A | 3/2017 |
| JP | 2017128796 | A | 7/2017 |
| KR | 1020050042974 | A | 5/2005 |
| KR | 1020080032896 | A | 4/2008 |
| KR | 1020160144492 | A | 12/2016 |
| KR | 1020180017592 | A | 2/2018 |

* cited by examiner

THERMAL DESORPTION ANALYSIS AUTOMATION SYSTEM AND ANALYSIS METHOD USING SAME

CROSS-REFERENCE TO RELATED APPLICATION

This application claims priority to Korean Patent Application No. 10-2022-0046079 filed Apr. 14, 2022, the disclosure of which is hereby incorporated by reference in its entirety.

BACKGROUND OF THE INVENTION

Field of the Invention

The following disclosure relates to a Thermal Desorption (TD) analysis automation system, and more particularly, to a TD analysis automation system including an automation system for quickly performing a wafer defect analysis process and an analysis method using the same.

Description of Related Art

Reactive gas used in a semiconductor manufacturing process is adsorbed to a surface of a membrane formed on a wafer and causes defects. Thermal Desorption (TD) analysis is used to analyze contaminants desorbed by thermally desorbing materials adsorbed to a surface of the wafer. Contaminant analysis has the advantage of being able to track in which process a wafer defect occurred. There are several methods for measuring contamination on a wafer. Compared with the analysis method using gas generated by the wafer inside FOUP and a method of spraying or contacting a solution on a surface of a wafer to collect and measure the solution, the TD analysis method showed similar results in general non-pattern wafer analysis, but showed strength in terms of pattern wafer analysis.

However, since the wafer is analyzed one by one, the time required is long. In addition, there is a possibility of a safety accident due to heat and gases inside a chamber in a heated state, and analysis is performed by replacing the wafer after cooling the chamber due to hot heat. As a result, there is a problem in that it takes additional cooling time and heating time, and it is not possible to quickly check whether or not the wafer is defective because the analysis may not be performed continuously.

Therefore, in the case of the TD analysis, an apparatus and method capable of reducing the required time are required.

SUMMARY OF THE INVENTION

An embodiment of the present invention is directed to providing a TD analysis automation system that uses a TD analysis method, but omits a cooling process of a chamber by constructing an automation system to reduce a required time, and an analysis method using the same.

Another embodiment of the present invention is directed to providing a TD analysis automation system in which a driving unit for moving a chuck up and down is disposed to penetrate through a chamber in order to reduce a size of a chamber, and an analysis method using the same.

Still another embodiment of the present invention is directed to providing a TD analysis automation system including a configuration for preventing ions from being adsorbed to a conduit during movement of a sampling gas and an analysis method using the same.

Yet another embodiment of the present invention is directed to providing a TD analysis automation system including a configuration for removing internal residual gas after sampling ends, and an analysis method using the same.

In one general aspect, a TD analysis automation system collecting and analyzing contaminants includes: a chamber that provides a space for heating a wafer; a heating device that includes a heater disposed inside the chamber and dissipating heat; an analysis device that is connected to a sampling port connected to the inside of the chamber and analyzes the contaminants sucked into the sampling port; a wafer transfer device that is provided with an arm; and a control unit that controls the wafer transfer device to insert the wafer into the chamber and transfer the wafer inside the chamber to the outside.

The TD analysis automation system may further include: a cover that is disposed inside the chamber and spaced apart from an inner surface of the chamber by a coupling member fixed to the chamber; and a chuck that is disposed facing the cover and moves up and down by a driving unit connected to the chamber, in which a disposition space in which a wafer may be disposed is formed between the cover and the chuck.

The TD analysis automation system may further include a load pin that has one end formed between the cover and the chuck and has the wafer disposed thereon, in which the other end of the load pin may be coupled to and disposed in the chuck or disposed to penetrate through a through hole formed in the chuck to be coupled to or in contact with the inner surface of the chamber.

The load pin may be disposed to penetrate through the chuck, and a cross-sectional area of an end portion of the load pin contacting the wafer may be formed larger than that of the through hole, and the end portion blocks the through hole by movement of the chuck.

The driving unit may be disposed to penetrate through the chamber, and driven by being connected to an external device disposed outside the chamber.

The chamber may include a cooling member disposed inside and outside an outer wall.

The TD analysis automation system may further include one or more gas ports that are disposed to penetrate through the chamber and inject an inert gas into the chamber.

One or more gas ports may be disposed between the cover and the chuck.

The sampling port may be connected to the analysis device by a conduit, the conduit may include a heating element that dissipates heat, and the heating element and the conduit may be connected to the control unit, and a temperature of the conduit may be controlled to a set temperature.

The analysis device may include a method of collecting contaminants in a solution and then analyzing the contaminants using chemical, physical, and electrical properties of the contaminants, a method of analyzing contaminants using light absorption and emission characteristics of the contaminants, a method of ionizing and analyzing contaminants, and a method of reacting an ionized material with contaminants and analyzing the contaminants.

In another general aspect, a TD analysis automation method using the TD analysis automation system includes: a wafer loading step of inserting, by a wafer transfer device, a wafer into a chamber through a predetermined movement and loading the wafer on one end of a load pin; a heating preparation step of moving, by a driving unit connected to the chamber, a chuck and disposing the chuck close to a cover spaced apart from an inner surface of the chamber; a wafer heating step of heating, by a heater disposed in the chamber, the wafer to desorb the contaminants; a sampling step of discharging the contaminants desorbed by the heating through a sampling port disposed to penetrate through the cover; and an analysis step of analyzing, by the analysis device, the sampled contaminants.

In the wafer heating step, a temperature of the heater may be controlled by measuring a temperature of the wafer in real time.

The TD analysis automation method may further include, after the sampling step, a ventilation step of supplying an inert gas into the chamber and discharging an internal gas through an outlet formed in the chamber.

The TD analysis automation method may further include, after the analysis step, a wafer replacement step of transferring, by a wafer transfer device, the sampled wafer to the outside of the chamber, and loading another wafer, in which the wafer replacement step may include a cooling step of transferring the heated wafer to the outside of the chamber and waiting outside the chamber for a predetermined time so that the heated wafer is naturally cooled.

The TD analysis automation method may further include, after the analysis step, a wafer replacement step of transferring, by the wafer transfer device, the sampled wafer to the outside of the chamber and loading another wafer, in which the wafer replacement step may include a cooling step of transferring the heated wafer to a cooling chamber disposed outside the chamber, and while the wafer is being cooled, another wafer may be transferred into the heating device and analyzed.

The TD analysis automation method may further include a chamber contamination level measurement step of supplying an inert gas into the chamber and measuring a contamination level inside the chamber by a second sampling port disposed to penetrate through the chamber.

DETAILED DESCRIPTION OF MAIN ELEMENTS

Figure 1:
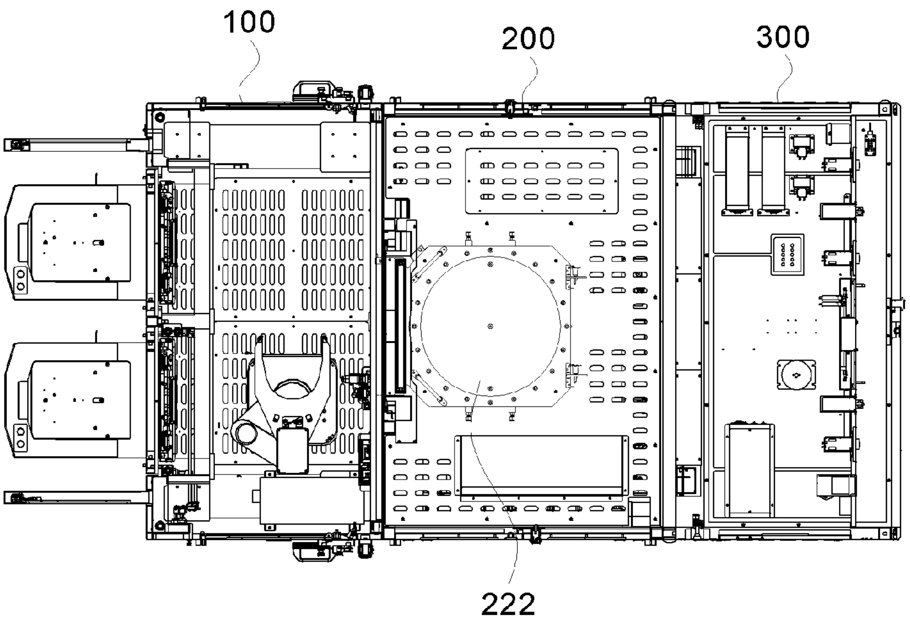
FIG. 1 is a configuration diagram of the present invention.

100: Wafer transfer device
200: Heating device
210: Gate
220: Chamber
221: Water inlet and outlet 222: Gas port
230: Cover 231: Coupling member
240: Chuck
241: Driving unit
250: Heater
260: Cooling member
300: Analysis device
310: Conduit
311: Sampling port
313: Valve
314: First vacuum pump
400: Collector
410: Second vacuum pump
242: Load pin
312: Heating element

DESCRIPTION OF THE INVENTION

An analysis system that analyzes thermally desorbed contaminants by heating a wafer is generally performed on one wafer, and has a disadvantage in that it takes time to replace the wafer after cooling a chamber due to hot heat and cool the wafer and a heating time is required.

The present invention proposes a TD analysis automation system configured as an automation system to reduce an operation time and an analysis method using the same.

Hereinafter, the TD analysis automation system according to the present invention having the configuration described above and an analysis method using the same will be described in detail with reference to the accompanying drawings.

The present invention may be variously modified and have several exemplary embodiments. Therefore, specific exemplary embodiments of the present invention will be illustrated in the accompanying drawings and be described in detail. However, it is to be understood that the present invention is not limited to a specific exemplary embodiment, but includes all modifications without departing from the scope and spirit of the present invention.

[1] Configuration of the Present Invention

FIG. 1 is an exemplary view of the present invention. Referring to FIG. 1, a wafer transfer device 100 for loading a wafer, a heating device 200 for heating the wafer to desorb contaminants, and an analysis device 300 for receiving and analyzing the desorbed contaminants are formed as one device.

The wafer transfer device 100, the heating device 200, and the analysis device 300 are formed as one device to prevent leakage of the gas used, and when the wafer is moved by the wafer transfer device 100, it is blocked from the outside to prevent contamination of the wafer.

The existing device cools the chamber due to hot air and then replaces the wafer, which takes a lot of time to cool and reheat the chamber. However, the present invention includes a coupling part coupled to the wafer, and has an advantage in that a wafer in a heated chamber may be replaced without a cooling process of the chamber by configuring the wafer transfer device 100 whose movement is programmed to transfer the wafer and the coupling part into or to the outside of the chamber. In this case, the coupling part and the wafer transfer device are made of a heat-resistant material with low thermal deformation, such as ceramic. The heated wafer is transferred to the outside of the chamber of the heating device 20, and separately cooled. The present invention has the advantage of continuously performing wafer defect analysis by omitting the cooling time of the chamber.

FIG. 1 is an exemplary view of the appearance of the present invention, and the appearance can be sufficiently changed, if necessary.

Figure 2:
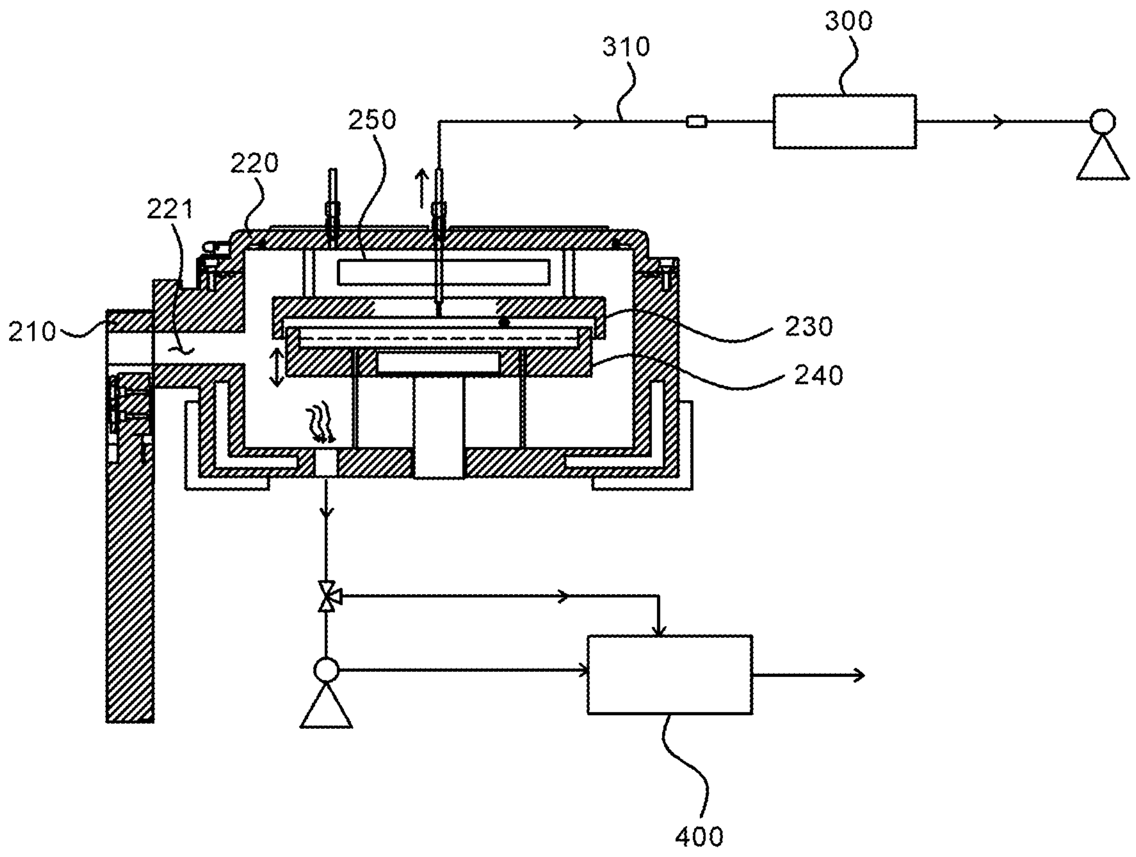
FIG. 2 is a detailed configuration diagram of the present invention.

FIG. 2 is a configuration diagram of the present invention. Referring to FIG. 2, the TD analysis automation system includes a heating device 200 that includes a chamber 220 providing a space for heating a wafer and a heater 250 disposed inside the chamber and dissipating heat, an analysis device 300 that is connected to a sampling port 311 connected to the inside of the chamber and analyzes contaminants sucked into the sampling port, a wafer transfer device 100 that is provided with an arm, and a control unit that controls the wafer transfer device to insert the wafer into the chamber and transfer the wafer in the chamber to the outside.

The heating device 200 is formed as the chamber 220 including the heater 250, and a gate 210 connected to a wafer transfer device is formed on one side. The wafer transfer device is disposed outside the chamber, includes a coupling part coupled to the wafer, passes through the gate 210 and a wafer inlet and outlet 221 by a built-in automation program, and transfers the wafer to the inside of the chamber 220 or transfers the wafer from the inside of the chamber 220 to the outside. The wafer seated inside the chamber 220 by the wafer transfer device is heated by the heater 250 disposed inside the chamber 220, and gas containing contaminants desorbed due to the heating moves to the analysis device 310 through the conduit 310. In this case, the control unit controls a temperature of the heater by receiving a temperature of components disposed inside the chamber in real time. A temperature measuring method uses the fact that the cover 230 and the chuck 240 are made of transparent quartz, and adjusts the heating temperature by measuring the temperature of the wafer in real time using an optical sensor disposed inside the chamber.

The analysis device 300 collects contaminants and analyzes ions. Through the ion analysis, it is easy to track in which process the defect of the wafer occurred. The analysis device 300 may adopt various analysis methods. For example, the analysis method includes a method of collecting contaminants in a solution and then analyzing the contaminants using chemical, physical, and electrical properties of the contaminants, a method of analyzing contaminants using light absorption and emission characteristics of the contaminants, a method of ionizing and analyzing contaminants, a method of reacting an ionized material with contaminants and then analyzing the contaminants, etc.

The heated and analyzed wafer is transferred to the outside of the chamber 220 by the wafer transfer device 100, and the residual gas in the chamber 220 is ventilated inside the chamber 220 by using a vacuum pump or injecting an inert gas. The gas discharged to the outside of the chamber 220 is discharged to the outside after the contaminants and gas are filtered by a collector 400.

The present invention may adopt a direct heating method and an indirect heating method as the heating method of the wafer. The direct heating method is a method of directly heating a wafer by disposing the wafer on a heating plate (not illustrated), and the indirect heating method uses a lamp or other heater to heat the wafer by methods such as conduction, convection, and radiation, without directly heating the wafer. In addition, the chuck 240 and the cover 230 may be made of transparent quartz, and light energy may penetrate into the wafer to heat the wafer.

In addition, a gate valve (not illustrated) is formed between the gate 210 and the water inlet and outlet 221, and the gate valve may be formed as a cooling type gate valve. The cooling type gate valve has a hole formed inside, and various cooling water is supplied through the hole to cool the gate valve so that it does not overheat. As the cooling water, PCW, UPW, CDA, etc., are used, and the type of cooling water used is not limited.

Figure 3:
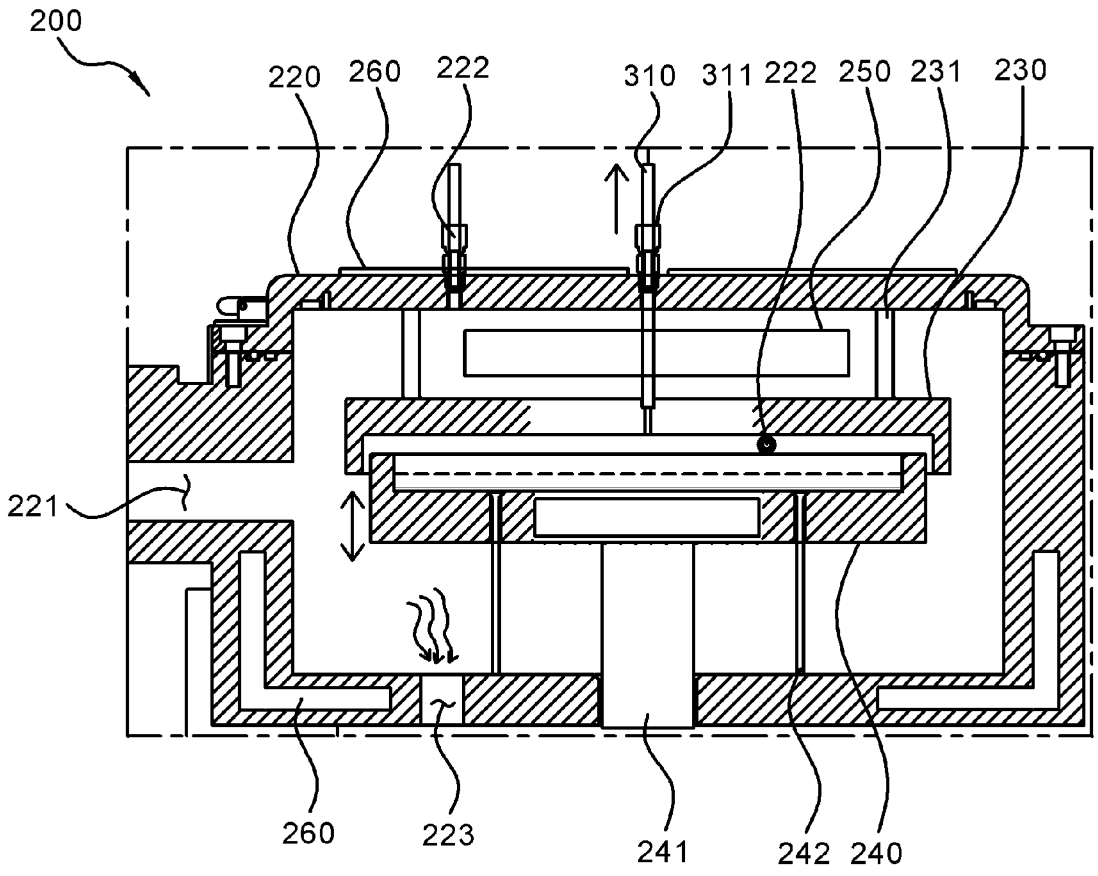
FIG. 3 is a chamber configuration diagram of the present invention.

FIG. 3 is a chamber configuration diagram of the present invention. Referring to FIG. 3, the TD analysis automation system includes a cover 230 disposed inside the chamber 220 and spaced apart from the inner surface of the chamber by a coupling member 231 fixed to the chamber 230 and a chuck 240 disposed to face the cover and moving up and down by a driving unit 241 connected to the chamber, in which a disposition space in which a wafer is disposed is formed between the cover and the chuck.

The heater 250 is illustrated as being disposed at an upper end in the chamber 220, but the position is not limited and may be formed in plural numbers.

The cover 230 is disposed in the center while being spaced apart from an inner surface of the chamber 220 by the coupling member 231. The coupling member 231 fixes the position of the cover 230 by coupling the outer surface of the cover 230 and the inner surface of the chamber 220. The cover 230 is provided with a hole to be connected to an analysis device, and a sampling port 311 is inserted into the hole to collect gas including contaminants desorbed from the wafer. An inner side surface of the cover may be formed in a predetermined shape so that the cover engages with the chuck 240.

The chuck 240 is disposed to face the cover 230 and moves up and down by the driving unit 241 coupled to the outer surface. A groove is formed on an inner side surface of the chuck 240 so that the wafer is disposed between the chuck 240 and the cover 230.

The driving unit 241 is disposed to penetrate through the chamber, and is connected to an external device disposed outside the chamber 220 to move up and down together with the chuck 240. The driving unit 241 moves by hydraulic pressure or pneumatic pressure. Since the driving unit is disposed to penetrate through the chamber, it is possible to reduce the overall volume of the chamber, and since the volume of the chamber is reduced, it is possible to reduce time and energy required for heating.

A load pin 242 is disposed so that a wafer is disposed between the cover 230 and the chuck 240. The load pin 242 is disposed between the chuck 240 and the cover 230 so that one end comes into contact with the wafer, and the other end of the load pin passes through the chuck 240 and is coupled to or in contact with the inner surface of the chamber 220. In addition, one end of the load pin 242 may be disposed between the chuck 240 and the cover 230 so as to come into contact with the wafer, and the other end thereof may be coupled to an inner side surface of the chuck 240. When the other end of the load pin is disposed to come into contact with the inner surface of the chamber, the load pin is supported by the chuck and may be spaced apart from the inner surface of the chamber as the chuck rises.

In addition, the load pin may be coupled with a separate driving unit so as to move up and down. By further including a separate driving unit, it is possible to control the transfer device to be stably seated on the load pin or the wafer disposed on the load pin to be stably seated on the transfer device.

This embodiment will be described with reference to the embodiment in which one end of the load pin 242 is disposed between the chuck 240 and the cover 230, and the other end thereof is coupled to the lower surface of the chamber 220 by penetrating through the chuck 240, as illustrated in drawings.

One or more cooling members 260 are disposed, and the heat generated by the heater 250 is disposed so that the components disposed outside the chamber 220 are not affected. The cooling member 260 is disposed inside the outer wall of the chamber 220, and may be disposed on an outer surface in contact with the frame if necessary.

The chamber 220 is provided with a gas port 222 into which an inert gas is injected. One or more gas ports 222 are disposed inside the chamber 220, and an inert gas is injected to discharge residual gas therein to the outside. The gas port 222 is connected to a valve and a mass flow controller (MFC) to control the supply amount of inert gas.

The gas port 222 is disposed between the chuck 240 and the cover 230 to spray an inert gas. The residual gas is discharged through an outlet 223 formed in the chamber 220. By periodically discharging the internal residual gas, safety accidents are prevented and accurate analysis is performed.

In addition, the inert gas may be supplied or stopped depending on the situation during the sampling of contaminants.

Figure 4:
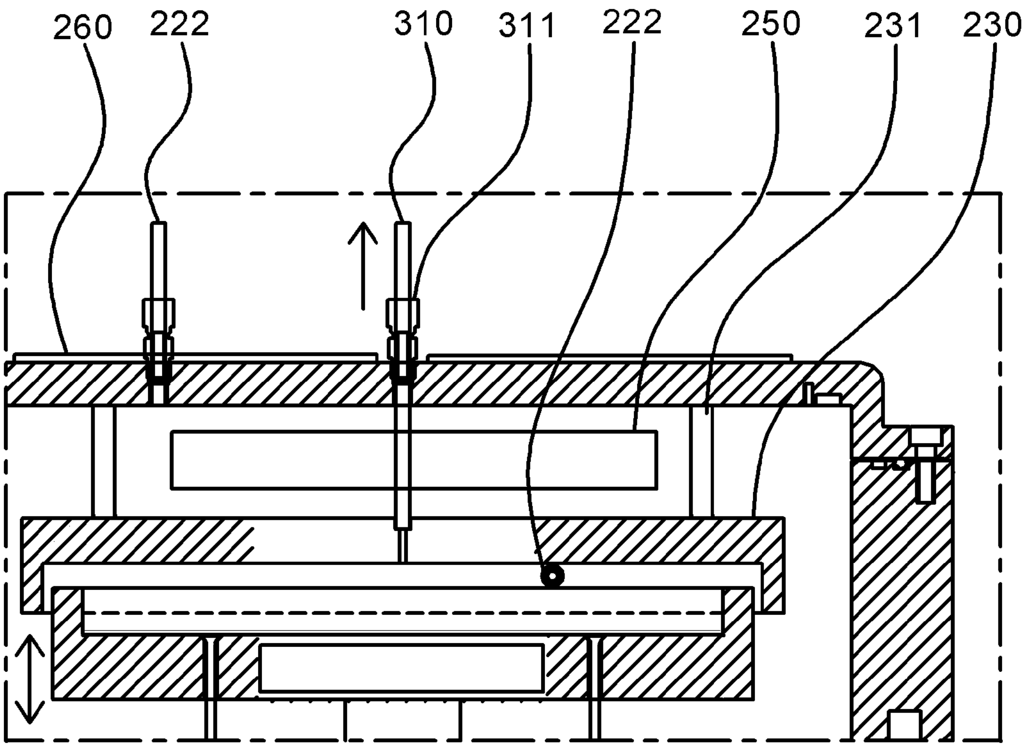
FIGS. 4 and 5 are enlarged views of FIG. 3.
Figure 5:
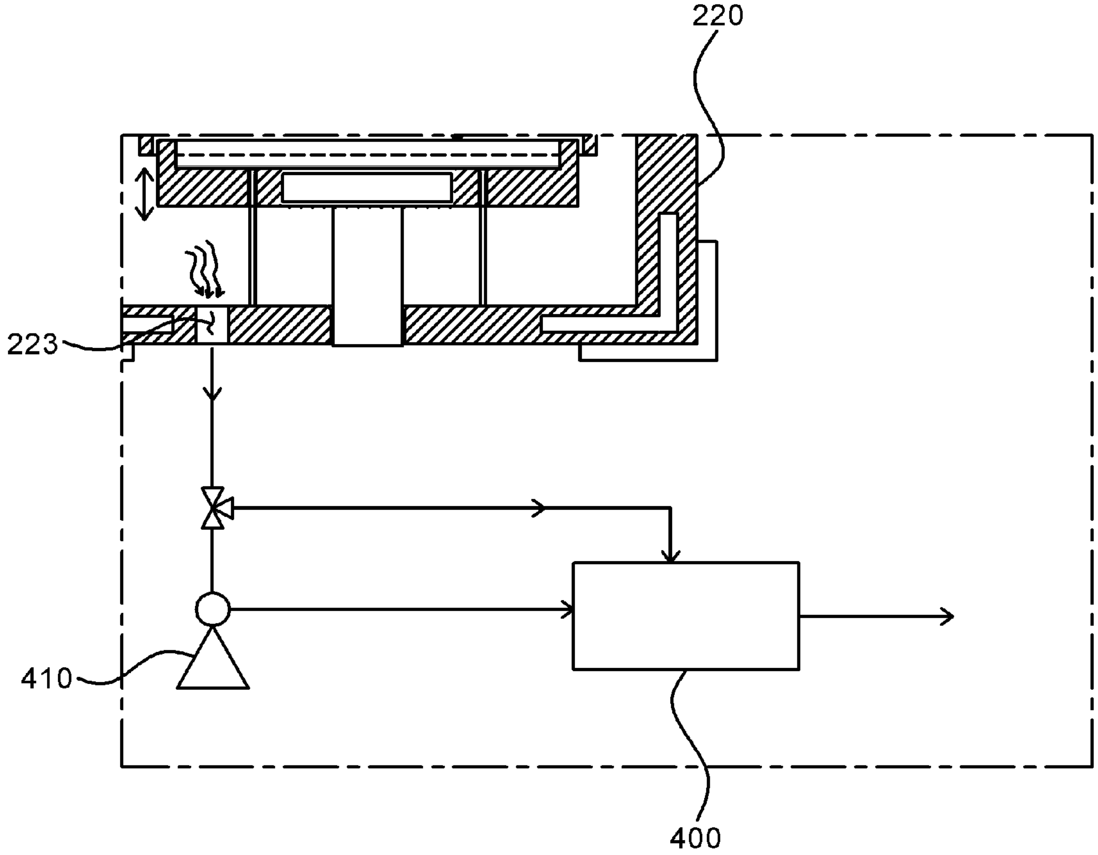

FIGS. 4 and 5 are enlarged views of FIG. 3. FIG. 4 is an enlarged view of the heating device 200 and enlarged view of a state in which a wafer is loaded. Referring to FIG. 4, the position of the cover 230 within the chamber 220 is fixed by the coupling member 231. The chuck 240 is raised by the driving unit 241, the load pin 242 on which the wafer is seated is inserted into the through hole of the chuck 240, and the wafer is disposed on the upper surface of the chuck 240.

The wafer is heated by the heater 250 in the chamber 220, and the contaminants desorbed by the heating are transferred to the analysis device 300 through the sampling port 311 coupled to penetrate through the upper side of the chamber 220. The sampling port 311 penetrates through the upper surface of the cover 230 or is fitted into a hole formed in the cover 230 to transfer gas including contaminants desorbed from the wafer.

The sampling port 311 is disposed to penetrate through the heater 250 or the heater 250 is disposed adjacent to the sampling port so that the sampled gas is not cooled when moving to the analysis device 300.

The chamber 220 includes the gas port 222 into which an inert gas is injected. After the heating and sampling steps end, the inert gas is injected to discharge the internal residual gas. A plurality of gas ports 222 are disposed in the chamber 220, and some of the gas ports 222 are disposed between the cover 230 and the chuck 240 to discharge the residual gas.

One end of the load pin 242 is disposed between the chuck 240 and the cover 230 and penetrates through the chuck 240 so that the other end thereof is coupled to the lower surface of the chamber 220. One end of the load pin 242 has a cross-sectional area larger than that of the through hole so that the load pin 242 may be stably disposed with the wafer. The load pin 242 is disposed to penetrate through a through hole 240-1 formed in the chuck 240, and the chuck 240 moves up and down by the driving unit 241 disposed on the outer side surface, and the load pin 242 is fixed to the inside of the chamber 220 and does not move.

In this case, the chuck 240 is raised by the driving unit 241, and the wafer disposed on the upper end of the load pin 242 is disposed on the upper surface of the chuck 240. An insertion groove into which an end of the load pin 242 is inserted is formed on an inner side surface of the chuck 240. The load pin 242 is disposed in the through hole 240-1, and the end portion of the load pin 242 is formed larger than the cross-sectional area of the through hole 240-1 to block the flow of gas.

Through this, the wafer is disposed between the chuck 240 and the cover 230, and the contaminants are desorbed by heating, but the end portion of the load pin 242 blocks the through hole 240-1 to prevent the contaminants from leaking into the through hole 240-1. In this case, the shape of the through hole, the shape of the end portion of the load pin, and the shape of the insertion hole into which the end portion of the load pin is inserted may be changed, and the load pin is made of the same material as the chuck to prevent damage due to thermal expansion.

FIG. 5 is a schematic diagram of residual gas discharged by the inert gas. Referring to FIG. 5, the outlet 223 is connected to a second vacuum pump 410 that sucks gas inside the chamber and the outside, and is connected to the collector 400 that purifies the discharged gas. After the heating and sampling, the inert gas is injected through one or more gas ports 222. The internal residual gas together with the injected inert gas is discharged to the outside of the chamber 220 through the outlet 223 formed in the chamber 220. The discharged gas is transferred through a gas discharge pipe, and discharged to the outside after the contaminants and gas are filtered by the collector 400. In addition, since the gas discharge pipe is connected to the second vacuum pump 410, there is an advantage in periodically ventilating the inside of the chamber 220.

Figure 6:
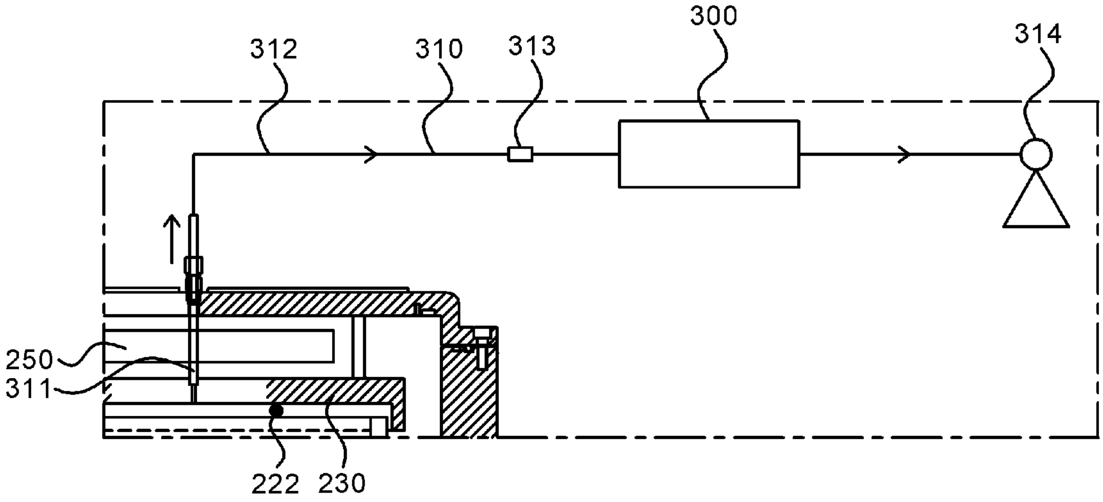
FIG. 6 is a schematic connection diagram of an analyzer.

FIG. 6 is a schematic diagram of a connection between the heating device and the analysis device. Referring to FIG. 6, the analysis device 300 may be connected to the heating device 200 to analyze contaminants desorbed from the wafer and measure the air in the chamber, if necessary.

The heating device 200 and the analysis device 300 are connected by a conduit 310 through which gas is transferred. The conduit 310 is fixed by the sampling port 311 disposed on the outer surface of the heating device 200. The sampling port 311 is disposed through the cover 230 inside the chamber 220. The wafer disposed between the cover 230 and the chuck is heated, and the desorbed contaminants are transferred to the analysis device through the sampling port. The contaminants may be transferred to the analysis device due to the increase in temperature inside the chamber, and may be transferred by the first vacuum pump 314 connected to the analysis device. It is determined whether the conduit 310 connecting the heating device and the analysis device is opened by the valve 313, and the amount of gas sucked into the analysis device 300 may be adjusted by a control unit controlling the valve 313.

In this case, the conduit 310 includes a heating element 312 that dissipates heat to prevent ions from being deposited in the conduit 310 due to the cooling when contaminants move to the analysis device 300. There is an effect of reducing analysis efficiency and memory by preventing ions from being deposited on the conduit 310. The heating element 312 and the conduit 310 are connected to the control unit, so the temperature of the conduit is controlled to a set temperature. The present invention does not limit the method of controlling the temperature of the conduit. For example, the heating element may be formed to surround a conduit and transfer heat to the conduit, and the conduit and heating element may be connected using a workpiece and other configuration, and then the temperature may be controlled by the temperature conducted to the workpiece.

In addition, it includes changing the shape of the conduit to maintain the set temperature. The duct is plumbed to the outside with a double pipe and then a heat source is connected to the double pipe to heat the air inside, thereby controlling the temperature of the conduit.

The present invention further includes a second sampling port (not illustrated) disposed through the chamber. The second sampling port is configured to connect the inside of the chamber and the analysis device in order to measure the contamination level in the chamber. The inert gas is supplied into the chamber, and the inert gas and contaminants are transferred to the analysis device together. It is possible to increase reliability by measuring the contamination level inside the chamber before the wafer analysis, and measure the exact amount of contaminants thermally desorbed from the wafer by measuring the amount of remaining contaminants after the heating of the wafer.

[2] Operation Flowchart of the Present Invention

The present invention includes an automation method using the TD analysis automation system described above.

The automation method includes a wafer loading step of inserting, by a wafer transfer device, a wafer into a chamber through a predetermined movement and loading the wafer on one end of a load pin; a heating preparation step of moving, by a driving unit, a chuck and disposing the chuck close to the cover; a wafer heating step of heating, by a heater disposed in the chamber, the wafer to desorb the contaminants; a sampling step of discharging the contaminants desorbed by the heating through a sampling port disposed to penetrate through the cover; and an analysis step of analyzing, by the analysis device, the sampled contaminants.

The wafer loading step includes loading a front opening unified pod (FOUP) in which a plurality of wafers are stored into a wafer transfer device (equipment front end module (EFEM)). The FOUP is a common configuration used to safely transfer silicon wafers in a controlled environment. The wafer transfer device mounts wafers in the FOUP one by one. The gate disposed on the outer surface of the chamber is opened, and the wafer is transferred into the chamber through the water inlet and outlet. The wafer is loaded on the upper end of the load pin, and the wafer transfer device moves to the outside of the chamber.

The heating preparation step is a step before heating the loaded wafer. The chuck moves up and down by the driving unit disposed on the outer side surface, and the wafer disposed on one end of the load pin is disposed on the inner surface of the chuck by the movement.

In this case, the load pin is disposed to penetrate through the chuck, and the end portion of the load pin is formed wider than the cross-sectional area of the through hole of the chuck, and the end portion of the load pin blocks the through hole by the movement of the moving unit.

In the wafer heating step, the heater in the chamber operates to heat the wafer. The loaded wafer is heated by external radiant heat between the chuck and the cover made of quartz. By heating, ions and organic materials on the surface of the wafer are vaporized and phase-changed into a gaseous form. The position of the heater is not limited to the upper and lower portions of the chamber, and a plurality of heaters may be disposed in the chamber. Although the analysis results vary depending on the heating time and holding time, it is preferable to maintain the temperature for 10 to 20 minutes after heating for 15 to 20 minutes on average.

In the sampling step, the contaminants desorbed by the heating are transferred to the analysis device through the sampling port. The inert gas may be introduced through a gas port disposed in the chamber and transferred to the analysis device by pressurization, and may be transferred through the first vacuum pump connected to the analysis device. The sampling port is disposed to penetrate through the cover, and it is most effective to suck gas when the sampling port is positioned on the upper end of the wafer.

Also, the sampling step may be performed according to the presence or absence of wafers in the chamber. Before the wafer loading step, the automation method includes a chamber contamination measurement step of supplying an inert gas into the chamber to measure the contamination level inside the chamber. It is possible to increase the reliability of the analysis by measuring the contamination level inside the chamber before performing the wafer analysis.

In this case, the control unit may supply or stop the inert gas when an emergency situation occurs during the sampling. The emergency situations include leakage, overheating, and excessive contamination. When gas leaks, the supply of inert gas is stopped, and when the waver overheats, the inert gas is supplied to cool the wafer.

In the analysis step, the sampled contaminants are analyzed. As the analysis method, a method of collecting contaminants in a solution and then analyzing the contaminants using chemical, physical, and electrical properties of the contaminants, a method of analyzing contaminants using light absorption and emission characteristics of the contaminants, a method of ionizing and analyzing contaminants, a method of reacting an ionized material with contaminants and then analyzing the contaminants, etc., may be applied.

The present invention includes a wafer replacement step of transferring, by the wafer transfer device, the sampled wafer to the outside of the chamber and loading another wafer. In the wafer replacement step, after the heating and sampling of the wafer loaded in the chamber are completed, the chuck is lowered by the driving unit and the wafer is disposed on the upper end of the load pin. The wafer disposed on the load pin is transferred to the outside of the chamber by the driving device, and another wafer is loaded into the chamber.

In this case, in the conventional TD analysis system, the cooling proceeds after one wafer is heated and analyzed as described above, but the present invention has an advantage of shortening the required time by omitting the chamber cooling to transfer the wafer through the automation system.

The wafer transferred to the outside of the heating device by the wafer transfer device is transferred to the FOUP, and the wafer is cooled during the transfer or transferred to the cooling device and loaded into the FOUP after being cooled.

The wafer replacement step includes a ventilation step to remove the residual gas inside the chamber. In the ventilation step, in order to remove the residual gas in the chamber, the wafer is transferred to the outside of the chamber, and then the inert gas is supplied while the gate is closed and sealed. The inert gas is supplied through the gas port disposed in the chamber, and the residual gas is discharged through an outlet formed on the lower surface of the chamber. The outlet is connected to a collection unit that collects solid or liquid particles in the gas, and is discharged to the outside after purification. In addition, the outlet is connected to the second vacuum pump to periodically restore the inside of the chamber to an initial state through vacuum pressure.

That is, during normal times and analysis, the exhaust using the inert gas is performed, and when cleaning is required, the air inside the chamber is rapidly discharged using the second vacuum pump.

The present invention includes a chamber contamination level measurement step of measuring the contamination level inside the chamber. In the chamber contamination level measurement step, the inert gas is supplied into the chamber, and the contamination level inside the chamber is measured by the second sampling port disposed to penetrate through the chamber.

The chamber contamination level measurement is performed according to the user's request regardless of the presence or absence of wafers and the progress step. By measuring the contamination level of the chamber before and after the disposition of the wafer, it is possible to check whether contaminants are introduced when the wafer is seated, and check the amount of contaminants remaining in the chamber by measuring before and after the heating of the wafer.

The present invention provides a method of cooling a heated wafer. During the ventilating step of the heated wafer, the inert gas is supplied into the chamber, and thus, the step of ventilating the inside of the chamber and the cooling step of cooling the heated wafer may be simultaneously performed.

In addition, the heated wafer is transferred to the outside of the chamber during the wafer replacement step, but may be naturally cooled by waiting outside the chamber for a certain period of time.

In addition, the wafer replacing step includes a cooling step of transferring the heated wafer to a cooling chamber disposed outside the chamber during the wafer replacement step, and another wafer may be transferred into the heating device while the wafer is being cooled and analyzed.

The present invention uses the TD analysis method, but has the effect of reducing a required time by constructing the automation system for transferring a wafer to omit a cooling process of a chamber and continuously supplying the wafer.

In addition, by arranging a driving unit for moving a chuck up and down outside the chamber, a size of the chamber is reduced, thereby reducing the time and energy required for heating the chamber.

In addition, since a conduit connecting a heating device and an analysis device includes a heating element, it is possible to maintain the conduit at a set temperature and prevent ions from being adsorbed to the conduit.

In addition, after the sampling is finished, optimal data can be derived by removing an internal residual gas through injection of an inert gas and suction of a vacuum pump.

The present invention is not limited to the above-mentioned exemplary embodiments, but may be variously applied, and may be variously modified without departing from the gist of the present invention claimed in the claims.

What is claimed is:

1. A Thermal Desorption analysis automation system collecting and analyzing contaminants, comprising:

a chamber configured to provide a space for heating a wafer;

a heating device including a heater disposed inside the chamber and configured to dissipate heat;

an analysis device connected to a sampling port communicating with an inside of the chamber and analyzes the contaminants sucked into the sampling port;

a wafer transfer device including an arm;

a control unit configured to control the wafer transfer device to insert the wafer into the chamber and transfer the wafer inside the chamber to an outside of the chamber;

a cover disposed inside the chamber and spaced apart from an inner surface of the chamber by a coupling member fixed to the chamber; and a chuck disposed to face the cover and configured to move up and down by a driving unit connected to the chamber, wherein a disposition space in which the wafer is disposed is formed between the cover and the chuck, wherein the driving unit is disposed to penetrate through the chamber and is driven by being connected to external equipment disposed outside the chamber, wherein the cover and the chuck are formed of a transparent material so that a temperature of the wafer disposed between the cover and the chuck is measured in real time, and wherein the control unit includes an optical sensor disposed inside the chamber and configured to measure the temperature of the wafer disposed between the cover and the chuck in real time.

2. The Thermal Desorption analysis automation system of claim 1, further comprising a load pin that has one end formed between the cover and the chuck and has the wafer disposed thereon, wherein a second end of the load pin is coupled to and disposed in the chuck or disposed to penetrate through a through hole formed in the chuck to be coupled to or in contact with the inner surface of the chamber.

3. The Thermal Desorption analysis automation system of claim 2, wherein the load pin is disposed to penetrate through the chuck, and a cross-sectional area of an end portion of the load pin contacting the wafer is formed larger than that of the through hole, and the end portion blocks the through hole by movement of the chuck.

4. The Thermal Desorption analysis automation system of claim 1, wherein the chamber includes a cooling member disposed inside and outside an outer wall.

5. The Thermal Desorption analysis automation system of claim 1, further comprising one or more gas ports that are disposed to penetrate through the chamber and inject an inert gas into the chamber.

6. The Thermal Desorption analysis automation system of claim 5, wherein one or more gas ports are disposed between the cover and the chuck.

7. The Thermal Desorption analysis automation system of claim 1, wherein the sampling port is connected to the analysis device by a conduit, the conduit includes a heating element that dissipates heat, and the heating element and the conduit are connected to the control unit, and a temperature of the conduit is controlled to a set temperature.

8. The Thermal Desorption analysis automation system of claim 1, wherein the analysis device includes a method of collecting contaminants in a solution and then analyzing the contaminants using chemical, physical, and electrical properties of the contaminants, a method of analyzing contaminants using light absorption and emission characteristics of the contaminants, a method of ionizing and analyzing contaminants, and a method of reacting an ionized material with contaminants and analyzing the contaminants.

9. A Thermal Desorption analysis automation method using the Thermal Desorption analysis automation system of claim 1, comprising:

a wafer loading step of inserting, by a wafer transfer device, a wafer into a chamber through a predetermined movement and loading the wafer on one end of a load pin;

a heating preparation step of moving, by a driving unit connected to the chamber, a chuck to move upward so that an upper portion of the chuck is inserted into a cover having an open lower side and disposed within the cover spaced apart from an inner surface thereof;

a wafer heating step of heating, by a heater disposed in the chamber, the wafer to desorb the contaminants;

a sampling step of discharging the contaminants desorbed by the heating through a sampling port disposed to penetrate through the cover; and an analysis step of analyzing, by the analysis device, the sampled contaminants, wherein, in the wafer heating step, a temperature of the wafer disposed between the cover and the chuck formed of the transparent material is measured in real time using the optical sensor disposed inside the chamber, and a temperature of the heater is controlled based on the measured temperature of the wafer.

10. The Thermal Desorption analysis automation method of claim 9, further comprising after the sampling step, a ventilation step of supplying an inert gas into the chamber and discharging an internal gas through an outlet formed in the chamber.

11. The Thermal Desorption analysis automation method of claim 9, further comprising after the analysis step, a wafer replacement step of transferring, by a wafer transfer device, the wafer to the outside of the chamber, and loading another wafer, wherein the wafer replacement step includes a cooling step of transferring the wafer to the outside of the chamber and waiting outside the chamber for a predetermined time so that the wafer is naturally cooled.

12. The Thermal Desorption analysis automation method of claim 9, further comprising after the analysis step, a wafer replacement step of transferring, by the wafer transfer device, the wafer to the outside of the chamber and loading another wafer, wherein the wafer replacement step includes a cooling step of transferring the wafer to a cooling chamber disposed outside the chamber, and while the wafer is being cooled, another wafer is transferred into the heating device and analyzed.

* * * * *